US00PP12321P2

(12) United States Plant Patent
van Veen

(10) Patent No.: US PP12,321 P2
(45) Date of Patent: Jan. 1, 2002

(54) DELPHINIUM PLANT NAMED 'MÈREL'

(75) Inventor: Jan G. van Veen, Noorden (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/639,901

(22) Filed: Aug. 16, 2000

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—C. A. Whealy

(57) ABSTRACT

A distinct cultivar of Delphinium plant named 'Mèrel', characterized by its upright plant habit; vigorous growth habit; strong flower stems; freely and continuous flowering habit; and large blue, purple and white semi-double flowers.

2 Drawing Sheets

BACKGROUND OF THE INVENTION

The present Invention relates to a new and distinct cultivar of Delphinium plant, botanically known as Delphinium hybrid, and hereinafter referred to by the cultivar name Mèrel.

The new Delphinium is a product of a planned breeding program conducted by the Inventor in a controlled environment in Noorden, The Netherlands. The new Delphinium was discovered and selected by the Inventor in a seed bed of sown seed from various crosses of unidentified Delphinium hybrid selections. The new Delphinium was selected in 1994 as an individual seedling on the basis of its numerous flowers and flower color.

Asexual reproduction of the new cultivar by cuttings harvested in Noorden, The Netherlands, has shown that the unique features of this new Delphinium are stable and reproduced true to type in successive generations.

SUMMARY OF THE INVENTION

Plants of the cultivar Mèrel have not been observed under all possible environmental conditions. The phenotype may vary somewhat with variations in environment such as temperatue, light intensity, daylength, irrigation amount and frequency, and fertilizer rate without, however, any variance in genotype.

The following traits have been repeatedly observed and are determined to be the unique characteristics of 'Mèrel'. These characteristics in combination distinguish 'Mèrel' as a new and distinct cultivar:

1. Upright plant habit.
2. Vigorous growth habit.
3. Strong flower stems.
4. Freely and continuous flowering habit.
5. Large blue, purple and white semi-double flowers.

BRIEF DESCRIPTION OF THE PHOTOGRAPHS

The accompanying colored photographs illustrate the overall appearance of the new Delphinium, showing the colors as true as it is reasonably possible to obtain in colored reproductions of this type. Colors in the photographs may differ slightly from the color values cited in the detailed botanical description which more accurately describe the actual colors of the new Delphinium.

The photograph on the left of the first sheet comprises a top perspective view of a typical flowering plants of 'Mèrel' grown in a container.

The photograph on the right of the first sheet comprises a close-up view of typical flowering stems of 'Mèrel'.

The photograph at the top of the second sheet is a close-up view of typical flowers of 'Mèrel'.

The photograph at the bottom of the second sheet is a close-up view of a typical flower and the upper surface of a typical leaf of 'Mèrel'.

DETAILED BOTANICAL DESCRIPTION

In the following description, color references are made to The Royal Horticultural Society Colour Chart except where general terms of ordinary dictionary significance are used. Plants used for the following description were about 12 months old and grown in containers under field conditions which closely approxiate commercial production conditions during the spring and summer in Noorden, The Netherlands.

Botanical classification: *Delphinium* hybrid cultivar Mèrel.
Parentage: Cross-pollination of unidentified selections of Delphinium hybrid, not patented.
Propagation:
- *Type cutting.*—By cuttings.
- *Rooting time.*—Cuttings develop roots in about 4 to 6 weeks at 15 to 20° C.
- *Root description.*—Fleshy.

Plant description:
- *Form.*—Upright perennial flowering plant with strong flowering stems that support numerous flowers. Appropriate for 17 to 21-cm containers.
- *Crop time.*—About 30 weeks are required to produce finished flowering plants in 12-cm containers.
- *Plant height.*—About 130 cm.
- *Plant diameter.*—About 40 cm.
- *Vigor.*—Vigorous.
- *Foliage description.*—Leaves simple, generally symmetrical, palmately-lobed, and long-persisting. Arrangement: Rosette at base and alternate along flowering stems. Quantity per flowering stem: About 13. Length: About 10 cm. Width: About 16 cm.

Shape: Deeply palmately-lobed. Apex: Acute to acuminate. Base: Reniform to hastate. Margin: Incised. Texture: Smooth; sparsely pubescent at veins on lower surface. Petiole: Length: About 11 cm. Diameter: About 3 by 4 mm. Color: Young foliage, upper surface: 137A. Young foliage, lower surface: 138B to 138C to 191B. Mature foliage, upper surface: 137B to 137C; veins, 137A. Mature foliage, lower surface: 138B; veins, 138B. Petiole color: 144B.

Flower description:

*Type/arrangement.*—Numerous semi-double flowers arranged on a raceme; zygomorphic. Not persistent.

*Quantity of flowers.*—Very freely flowering. Main flowering stems, about 60 flowers; secondary flowering stems, about 25 flowers; about 140 flowers per plant typically develop during the flowering season.

*Natural flowering season.*—Summer to late summer; flowering continuous during this period.

*Fragrance.*—Very faint, dull.

*Individual flower longevity on the plant.*—About two or three days.

*Flowering stem longevity as a cut flower.*—About 10 days.

*Flower buds* (*about 2 or 3 days before opening*).—Length: About 2 cm. Diameter: About 1.2 cm. Shape: Orbicular to obovate. Color: Pale blue, 97A, paler blue towards the base.

*Flower size.*—Diameter: About 6 cm. Depth, excluding spur: About 1.2 cm. Spur length: About 1.8 cm.

*Petals.*—Quantity: About 19 per flower. Length: About 3.4 cm. Width: About 1.7 cm. Shape: Obovate to oblanceolate. Apex: Acute to obtuse or dentate. Margin: Entire. Texture: Slightly rugose; dull. Color: When opening, upper surface: Margins, 98A to 100A, surrounding central stripe, 75A. When opening, lower surface; Margins, 98A, surrounding central stripe, 75A. Fully opened, upper surface: 98A to 98B. Fully opened, lower surface: 98B to 98D.

*Petaloids.*—Origin: Stamenoidal. Quantity: About 8 per flower. Length: About 1.7 cm. Width: About 9 mm. Shape: Spatulate to flabellate. Apex: Dentate. Margin: Entire. Texture: Slightly rugose; dull. Color: When opening, both surfaces: Margins, white, close to 155D; central stripe, towards base, 75A, towards apex, 98A. When opening, lower surface: Margins, white, close to 155D; central stripe, 98C to 98D.

*Calyx.*—Sepal quantity: Five. Length: About 1.1 cm. Width: About 6 mm. Sepal shape: Linear. Sepal apex: Acute. Sepal margin: Entire. Sepal texture: Smooth, dull. Sepal color, both surfaces: 143B.

*Pedicel.*—Length: About 6.5 cm. Angle: About 20 to 30° from vertical. Strength: Moderate to strong. Color: 138A to 138B.

*Peduncle.*—Length: About 130 cm. Diameter: About 3 mm. Strength: Very strong. Aspect: Mostly upright. Texture: Glabrous; somewhat glaucous towards the base. Color: 138A to 138B.

*Reproductive organs.*—Stamens: Quantity: About 20. Anther shape: Oblong, basifixed. Anther length: About 2 mm. Anther color: 138B. Pollen amount: Scarce, gray. Pistils: Quantity: Five. Pistil length: About 1 cm. Style length: About 8 mm. Style color: 138A to 138B.

*Seed description.*—Length: About 2 mm. Diameter: About 2 mm. Color: Dark brown to almost black, close to 202A.

Pest Disease resistance: Plants of the new Delphinium have been noted to be somewhat resistant to pathogens and pest common to Delphinium.

It is claimed:

1. A new and distinct cultivar of Delphinium plant named 'Mèrel', as illustrated and described.

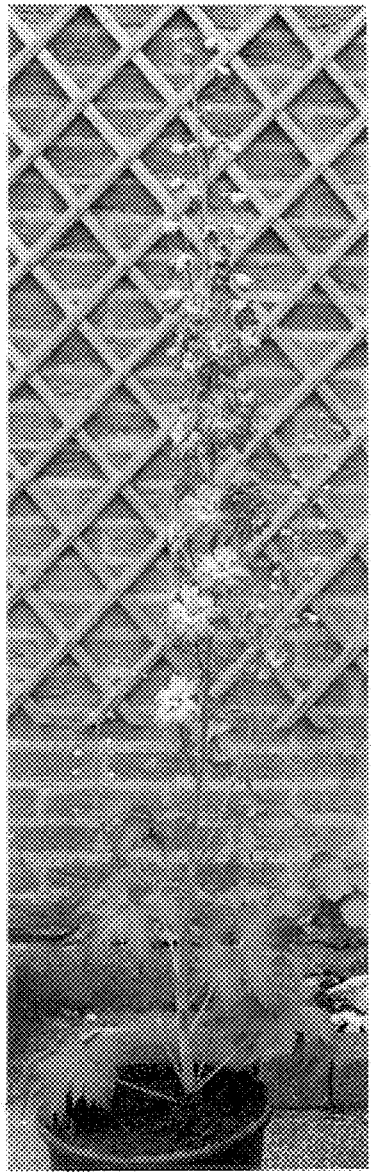
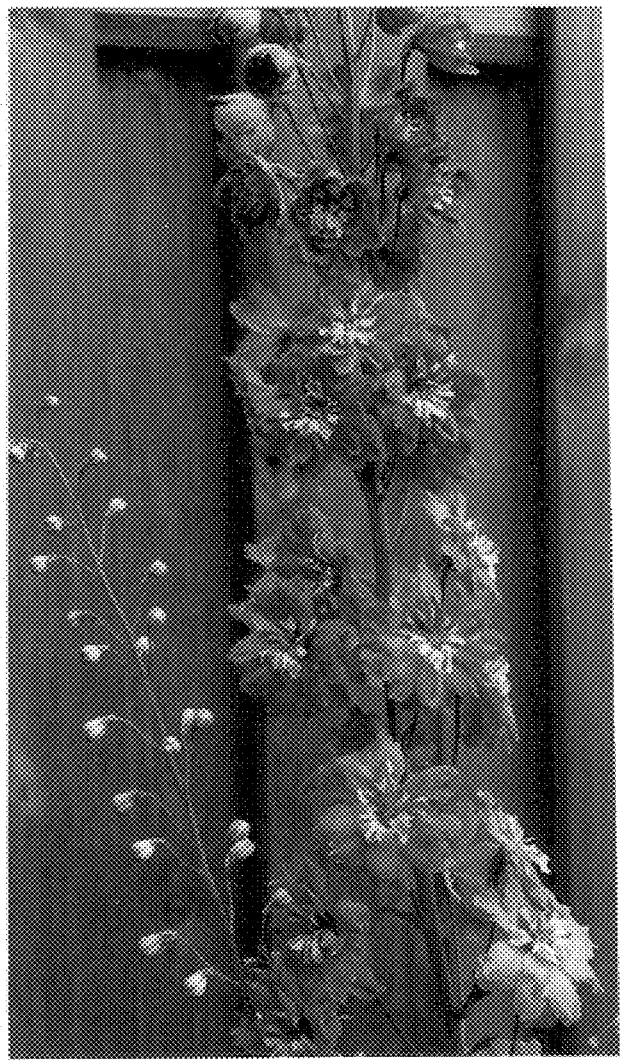

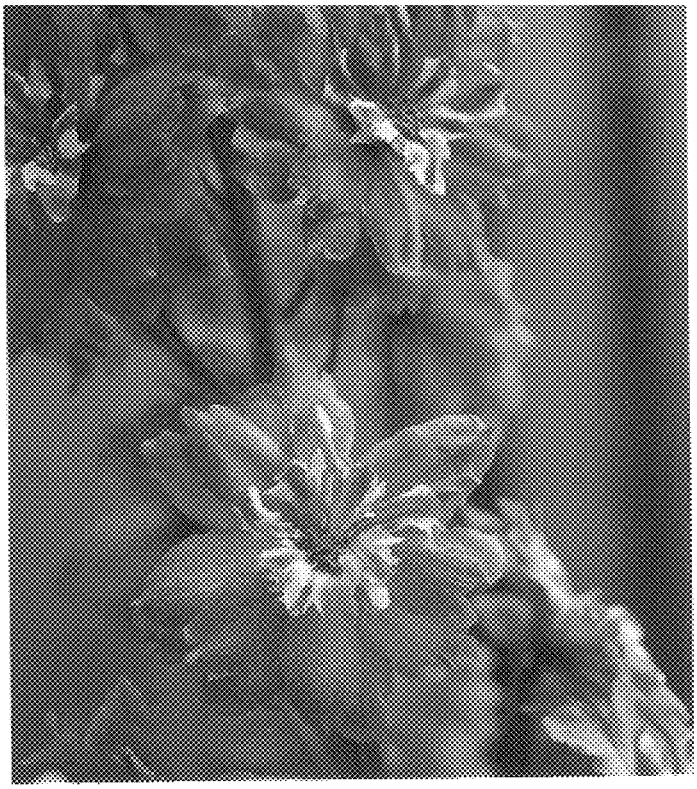
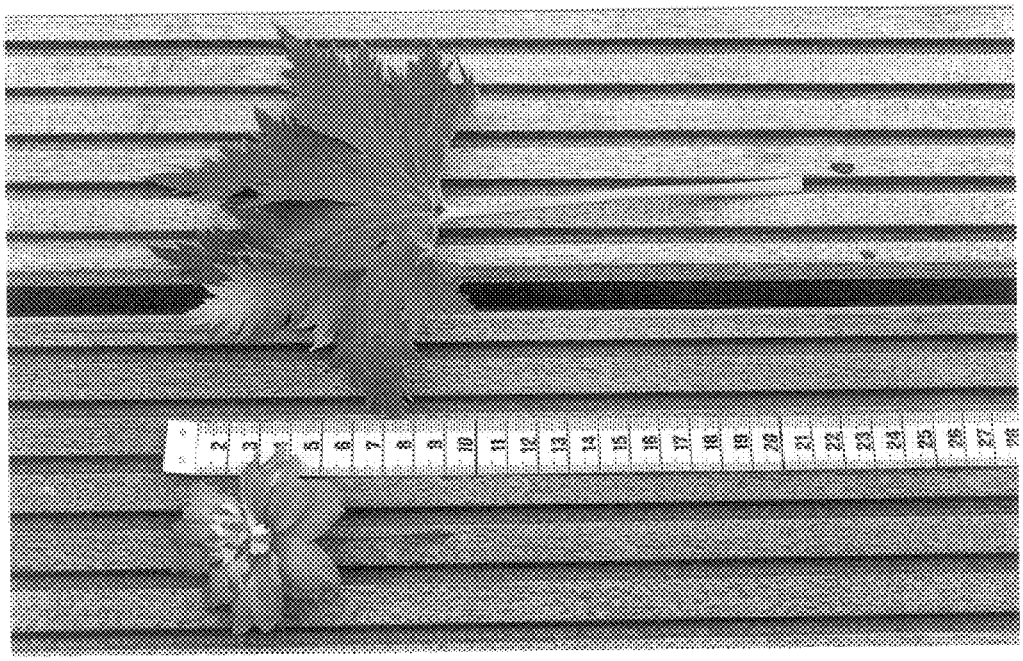

* * * * *